US012424315B2

United States Patent
Nix et al.

(10) Patent No.: US 12,424,315 B2
(45) Date of Patent: Sep. 23, 2025

(54) VENTRICULAR ASSIST DEVICE (71) Applicant: Abiomed Europe GmbH, Aachen (DE)

(72) Inventors: Christoph Nix, Aachen (DE); Katrin Lunze, Aachen (DE); Thorsten Siess, Aachen (DE); Walid Aboulhosn, Aachen (DE)

(73) Assignee: Abiomed Europe GmbH, Aachen (DE)

( * ) Notice: Subject to any disclaimer, the term of this patent is extended or adjusted under 35 U.S.C. 154(b) by 67 days.

(21) Appl. No.: 17/851,127

(22) Filed: Jun. 28, 2022

(65) Prior Publication Data

US 2023/0048736 A1  Feb. 16, 2023

Related U.S. Application Data (63) Continuation of application No. 16/327,104, filed as application No. PCT/EP2017/070953 on Aug. 18, 2017, now Pat. No. 11,413,444.

(30) Foreign Application Priority Data

Aug. 23, 2016 (EP) .................................. 16185397

(51) Int. Cl.
*A61M 60/122* (2021.01)
*A61M 60/135* (2021.01)
(Continued)

(52) U.S. Cl.
CPC .......... *G16H 40/63* (2018.01); *A61M 60/135* (2021.01); *A61M 60/148* (2021.01);
(Continued)

(58) Field of Classification Search
CPC ..... A61M 1/101; A61M 1/1005; A61M 1/122
See application file for complete search history.

(56) References Cited

U.S. PATENT DOCUMENTS 7,010,954 B2   3/2006  Siess et al.
7,841,976 B2  11/2010  McBride et al.
(Continued)

FOREIGN PATENT DOCUMENTS

CN  101513545 A   8/2009
CN  201572358 U   9/2010
(Continued)

OTHER PUBLICATIONS

Office Action for corresponding CN Application No. 201880053604.9 dated Jun. 27, 2022, (22 pages).
(Continued)

*Primary Examiner* — Michael J D'Abreu
(74) *Attorney, Agent, or Firm* — BOTOS CHURCHILL IP LAW LLP (57) ABSTRACT

A control device (100) for controlling the rotational speed ($n_{VAD}(t)$) of a non-pulsatile ventricular assist device, VAD, (50) uses an event-based within-a-beat control strategy, wherein the control device is configured to alter the rotational speed of the VAD within the cardiac cycle of the assisted heart and to synchronize the alteration of the rotational speed with the heartbeat by at least one sequence of trigger signals ($\sigma(t)$) that is related to at least one predetermined characteristic event in the cardiac cycle. Further, a VAD (50) for assistance of a heart comprises the control device (100) for controlling the VAD, wherein the VAD is preferably a non-pulsatile rotational, for example catheter-based, blood pump.

19 Claims, 5 Drawing Sheets

(51) Int. Cl.
*A61M 60/148* (2021.01)
*A61M 60/178* (2021.01)
*A61M 60/205* (2021.01)
*A61M 60/216* (2021.01)
*A61M 60/414* (2021.01)
*A61M 60/422* (2021.01)
*A61M 60/50* (2021.01)
*A61M 60/562* (2021.01)
*A61M 60/569* (2021.01)
*A61M 60/816* (2021.01)
*A61M 60/857* (2021.01)
*G16H 40/63* (2018.01)
*G16H 50/30* (2018.01)

(52) U.S. Cl.
CPC ........ *A61M 60/178* (2021.01); *A61M 60/205* (2021.01); *A61M 60/216* (2021.01); *A61M 60/414* (2021.01); *A61M 60/422* (2021.01); *A61M 60/50* (2021.01); *A61M 60/562* (2021.01); *A61M 60/569* (2021.01); *A61M 60/816* (2021.01); *A61M 60/857* (2021.01); *G16H 50/30* (2018.01); *A61M 2205/3334* (2013.01); *A61M 2205/3365* (2013.01); *A61M 2205/50* (2013.01); *A61M 2230/04* (2013.01); *A61M 2230/30* (2013.01)

(56) References Cited

U.S. PATENT DOCUMENTS

| | | | |
|---|---|---|---|
| 9,125,977 | B2 | 9/2015 | Nishimura et al. |
| 9,757,502 | B2 | 9/2017 | Burke et al. |
| 10,632,240 | B2 | 4/2020 | Yomtov |
| 2003/0045772 | A1* | 3/2003 | Reich ................ A61M 60/216 600/18 |
| 2005/0071001 | A1 | 3/2005 | Jarvik |
| 2005/0215843 | A1 | 9/2005 | Medvedev |
| 2009/0138080 | A1 | 5/2009 | Siess et al. |
| 2011/0054239 | A1* | 3/2011 | Sutton ................ A61M 60/419 600/16 |
| 2011/0178361 | A1 | 7/2011 | Yomtov |
| 2013/0138205 | A1 | 5/2013 | Kushwaha et al. |
| 2014/0323796 | A1 | 10/2014 | Medvedev et al. |
| 2015/0246166 | A1 | 9/2015 | Greatrex et al. |
| 2016/0101230 | A1* | 4/2016 | Ochsner ................ A61B 5/6869 604/4.01 |
| 2017/0112985 | A1* | 4/2017 | Yomtov ................ A61B 5/316 |

FOREIGN PATENT DOCUMENTS

| | | |
|---|---|---|
| CN | 104721897 A | 6/2015 |
| CN | 104822400 A | 8/2015 |
| CN | 104971389 A | 10/2015 |
| CN | 105246522 A | 1/2016 |
| EP | 2298375 A1 | 3/2011 |
| JP | H01297073 A | 11/1989 |
| JP | 2003500117 A | 1/2003 |
| JP | 2004073875 A | 3/2004 |
| JP | 2004515278 A | 5/2004 |
| JP | 2004526546 A | 9/2004 |
| JP | 2008536554 A | 9/2008 |
| JP | 2009297174 A | 12/2009 |
| KR | 20140123042 A | 10/2014 |
| WO | 9917819 A1 | 4/1999 |
| WO | 0071184 A1 | 11/2000 |
| WO | 02094348 A1 | 11/2002 |
| WO | 2005006975 A1 | 1/2005 |
| WO | 2009019017 A2 | 2/2009 |
| WO | 2010099411 A1 | 9/2010 |
| WO | 2011090927 A1 | 7/2011 |
| WO | 2013184932 A1 | 12/2013 |
| WO | 2015040222 A2 | 3/2015 |
| WO | 2015179921 A1 | 12/2015 |

OTHER PUBLICATIONS

Office Action from corresponding Korean Application No. 10-2019-7008466 dated Nov. 21, 2022 (10 pp.).
Office Action for corresponding Chinese Patent Application No. 201780051986.7 dated Sep. 13, 2021 (14 pages).
Office Action for corresponding Japanese Application No. 2019-507901 dated Aug. 3, 2021 (14 pages).
First Office Action from corresponding Chinese Patent Application No. 202210307536.2 dated Feb. 28, 2025 (14 pp.).

* cited by examiner

VENTRICULAR ASSIST DEVICE

CROSS-REFERENCE TO RELATED APPLICATIONS

The present application is a continuation of U.S. application Ser. No. 16/327,104, filed Feb. 21, 2019, now allowed, which is a national phase entry under 35 U.S.C. § 371 of International Application No. PCT/EP2017/070953 filed Aug. 18, 2017, published in English, which claims priority from European Patent Application No. 16185397.3, filed Aug. 23, 2016, all of which are incorporated herein by reference.

FIELD OF THE INVENTION

The present invention concerns the field of non-pulsatile ventricular assist devices (VAD). In particular, the invention relates to a control device for within-a-beat control of a non-pulsatile VAD, such as an intravascular rotary blood pump, and a VAD comprising the control device for controlling the VAD.

BACKGROUND OF THE INVENTION

If the pumping function of a patient's heart is insufficient despite optimal medical treatment, the circulatory system can be assisted by a VAD. VADs may assist or even substitute the insufficient ventricular pumping function of a heart by delivering blood parallel to the ventricle of the heart. To this end, a VAD typically is configured to take blood from the blood circulation at an inlet to eject it back to the blood circulation at an outlet. In doing so, the VAD needs to overcome the pressure difference between the outlet and the inlet, i.e. between after-load and pre-load of the VAD.

One particular example of a VAD is a catheter-based rotary blood pump that is arranged to be placed or implanted directly into the heart for several hours or days for assisting the heart function until recovery. U.S. Pat. No. 5,911,685 A discloses an exemplary intravascular rotary blood pump. However, there are other types of VADs as well.

In patients receiving heart assistance by a non-pulsatile blood pump, an increased tendency to bleeding has been observed. The increased tendency to bleeding has been associated with a deficit in a particular blood glycoprotein known as von Willebrand factor (vWF) that is involved in hemostasis.

The term "cardiac cycle" used herein embraces the dynamic behavior of the heart during one heartbeat including e.g. the time-dependent changes of blood pressure and ventricular volume. The heartbeat herein is defined to start with the evocation of the atrial contraction, and to end right before the following atrial contraction, distinguishing between systole and diastole. The systole of the heart (also called the ejection phase of the heart) is the phase between the closing of the mitral valve and the closing of the aortic valve. The diastole (also called the filling phase of the heart) is the phase between the closing of the aortic valve and the closing of the mitral valve. The frequency of the heart passing through the cardiac cycle is known as the heart rate.

SUMMARY OF THE INVENTION

It is an object of the present invention to provide an improved assistance to the circulatory system of a patient by which the above-observed vWF deficiency can be avoided or at least reduced.

In particular, it is an object of the present invention to provide a smart control device for a VAD, such as a rotary blood pump, which operates the VAD with the aim of avoiding or at least reducing the side effect of applying a non-pulsatile VAD resulting in vWF deficiency.

In particular, it is a further object of the present invention to provide a smart control device for a VAD which operates the VAD so that, besides avoiding or at least reducing the side effect of the application of a non-pulsatile VAD, a required blood pressure is provided, which is related to the patient's current perfusion demands.

It has been found by the inventors that when a minimum residual pulsatility of the blood pressure is restored and/or maintained in the circulatory system, the above-discussed increased tendency to bleeding is reduced. Additionally, a sufficient pressure pulsatility also seems supportive of a sufficient perfusion of the microvasculature of the circulatory system.

Thus, the main idea of the present invention is an event-based within-a-beat control strategy which extends a control loop for the rotational speed of the VAD by a speed command signal generator for generating a speed command signal for the alteration of the rotational speed of the VAD, so that a predetermined desired minimum pulsatility is achieved either in a first setup by an open-loop control, wherein the speed command signal is alternated between predefined rotational speed levels or in a second setup by a closed-loop pressure control in a feedback system, wherein the speed command signal is automatically set for each heartbeat by an additional outer pressure control loop resulting in a cascade control.

The proposed event-based within-a-beat control strategy for the blood pressure, in one particular embodiment, enables the pulsatility of the patient's blood pressure to be affected by changing the blood flow through the VAD within a cardiac cycle of the heart. One particular application of this event-based within-a-beat control strategy for the blood pressure can be to restore and/or maintain the desired minimum pulsatility of the arterial blood pressure, thus avoiding the assumed side effect of the VAD application on the vWF release. This is supported by the fact that it has been observed that most continuous flow VADs reduce the pulsatility and thus lead to reduced vWF appearance.

Thus, the event-based within-a-beat control strategy proposed herein for the rotational speed of the VAD is particularly useful for avoiding the inherent side effect of non-pulsatile VADs with respect to vWF deficiency. In other words, the particular proposed speed alteration for restoration and/or maintenance of a desired minimum pulsatility of the blood pressure is not considered as a therapy but rather as a feature for eliminating the inherent side effect of non-pulsatile VADs.

Moreover, the alteration of the pump speed within a cardiac cycle (hereinafter also referred to as "heartbeat" or "beat") generates further advantageous effects compared to non-pulsatile heart assistance, such as improved perfusion of the microvasculature of the circulatory system.

In the context of restoring and/or maintaining the desired minimum pulsatility of the arterial blood pressure, the term "pulsatility" used herein is generally understood as the difference $$\Delta AoP(h) = AoP|_{max}(h) - AoP|_{min}(h)$$

between the maximum aortic pressure $AoP|_{max}(h)$ and the minimum aortic pressure $AoP|_{min}(h)$ during the $h^{th}$ cardiac cycle.

In the following, for the sake of simplification, all characteristic measurement values and calculated values will just be referenced to a concrete $(j-1)^{st}$, $j^{th}$, $(j+1)^{st}$, and so on, heartbeat or a more general $h^{th}$ heartbeat, which also implies the dependence of the values on continuous time t and on concrete measurement points k. For example, $$\text{AoP}|_{max}(j) = \max_k\{\text{AoP}(t_{j,k})\} \text{ for } k=0 \ldots m_j$$

with the index j indicating the $j^{th}$ heartbeat, and the maximum of the signal AoP is calculated for the $j^{th}$ heartbeat over all $k=0 \ldots m$; measurement values of the signal AoP starting with the first measurement point of the $j^{th}$ heartbeat $k=0$, and ending with the last measurement point $k=m_j$ right before the next $(j+1)^{st}$ heartbeat starts. Then $$\text{AoP}|_{max}(j+1) = \max_k\{\text{AoP}(t_{j+1,k})\} \text{ for } k=0 \ldots m_{j+1}$$

and so on.

Figure 3:
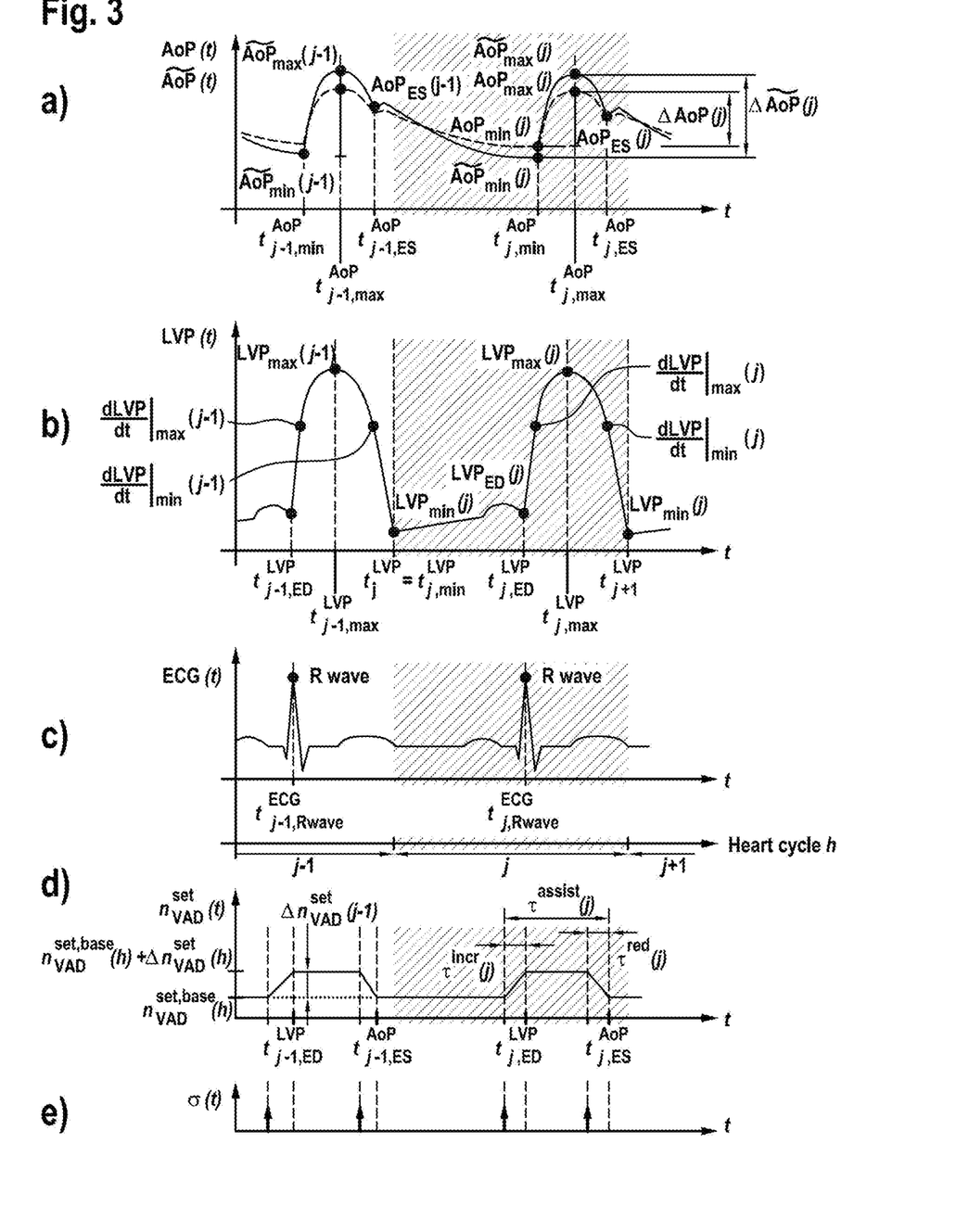
FIG. 3 shows a diagram with exemplary signal waveforms that represent, a) the aortic pressure (AoP(t)), b) the left ventricular pressure (LVP(t)), c) an ECG (ECG(t)), and d) a speed command signal trajectory ($n_{VAD}^{set}$(t)), and with e) a corresponding sequence of trigger signals (σ(t)), for illustrating the principle of pulsatile speed control to restore and/or maintain blood pulsatility by means of the VAD of FIGS. 1 and 2 under control of the control device of FIG. 1.

The inventors assume that restoration and/or maintenance of a minimum residual pulsatility is desirable, particularly in the case of a VAD-assisted circulatory system. Accordingly, the main idea of this invention is to improve the control of a non-pulsatile VAD so that during the cardiac cycle, i.e. within one heartbeat, the rotational speed $n_{VAD}(t)$ of the VAD is altered so that a desired minimum pulsatility $\Delta \widetilde{\text{AoP}}$ (h) is generated which is intended to restore and/or maintain a minimum residual pulsatility in the artery of interest, i.e. in the aorta in the case of left-sided heart assistance. The definitions of different types of pulsatility are as follows (see also FIG. 3a)):

Physiologic (non-assisted) pulsatility: $\Delta\text{AoP}(h) = \text{AoP}|_{max}(h) - \text{AoP}|_{min}(h)$ Desired (assisted) minimum pulsatility: $\Delta\widetilde{\text{AoP}}(h) = \text{AoP}|_{max}(h) - \text{AoP}|_{min}(h)$ Pulsatility difference: $\Delta\text{AoP}_{pulse}(h) = \Delta\widetilde{\text{AoP}}(h) - \Delta\text{AoP}(h)$ Accordingly, the desired minimum pulsatility $\Delta\widetilde{\text{AoP}}$ (h) depends on the maximum and minimum desired aortic pressure $\widetilde{\text{AoP}}|_{max}$ (h) and $\widetilde{\text{AoP}}|_{min}$ (h), respectively, within the h cardiac cycle. The pulsatility difference $\Delta\text{AoP}_{pulse}(h)$ is defined to be the difference between the current physiologic (non-assisted) pulsatility $\Delta\text{AoP}(h)$ and the desired (assisted) minimum pulsatility $\Delta\widetilde{\text{AoP}}$ (h).

In this regard, the inventors have further found that predetermined values for the desired minimum pulsatility are in the range of $\Delta\widetilde{\text{AoP}}$ (h)=[15 . . . 30] mmHg, but the desired minimum pulsatility $\Delta\widetilde{\text{AoP}}$ (h) may be higher, as well.

One further point found by the inventors is that a physical prerequisite that preferably has to be fulfilled by the VAD to be used for the herein disclosed applications is the absence of relevant inertia. That is to say, the VAD is preferably a low inertia device. Up to now, rotary blood pumps, for example, such as the above-mentioned catheter-based pump, which have a negligibly small mass moment of inertia are perfectly suited for speed control scenarios with within-a-beat speed alterations, whilst being highly energy efficient, e.g. avoiding thermal dissipation losses. Particular characteristics for achieving the VAD having a small mass moment of inertia are, inter alia, i.e. not exclusively, moving, in particular rotating, parts of the VAD comprise low masses, for example a rotor or impeller may be made of a low weight material, such as plastic materials, synthetic materials or the like; a driving means, such as an electric motor, is arranged near, preferably very near, most preferably adjacent, to the rotor or impeller, so that a shaft coupling the motor with the rotor or impeller can be kept short, thereby keeping the rotating mass thereof low (for instance, devices are known that have a rotating drive cable or wire for coupling a rotor to the motor, which would be undesirable as the mass of the cable or wire increases the mass to be accelerated or decelerated); all moving, in particular rotating, parts have small diameters, so that the resulting mass moment of inertia of the parts can be kept small.

A first aspect of the invention provides a control device which alters the rotational speed (in the following just "speed") $n_{VAD}(t)$ of a non-pulsatile VAD within a cardiac cycle with respect to physiological conditions in an event-based manner.

To this end, the control device can be configured to alter the speed of the VAD within a cardiac cycle of the assisted heart and, in combination with a trigger signal generator, to synchronize the alteration of a speed command signal $n_{VAD}(t)$ for speed with the heartbeat by using at least one event sequence that is related to at least one predetermined characteristic recurring event within the cardiac cycle. Thus, the native cardiac output of the assisted heart can be affected by the VAD-induced blood flow $Q_{VAD}(t)$.

In a particular embodiment, the control device may be configured to adjust the speed command signal $n_{VAD}^{set}(t)$ for either a predetermined pulse duration $\tau^{pulse}(h)$ or a heart rate dependent pulse duration $\tau^{assist}(h)$ compared to a basic speed level $n_{VAD}^{set,\ basic}(h)$ to generate a desired minimum pulsatility $\Delta\text{AoP}(h) = \Delta\widetilde{\text{AoP}}(h)$ in an artery of interest by the resulting blood flow through the VAD within the $h^{th}$ cardiac cycle.

An artery of interest may be at least the aorta, if the VAD is configured for left-sided heart assistance. Alternatively, an artery of interest may be at least the pulmonary artery, if the VAD is configured for right-sided heart assistance.

To this end, the control device may be configured to adjust the speed command signal $n_{VAD}^{set}(t)$ of the VAD and to control the speed $n_{VAD}(t)$ of the VAD satisfying the desired minimum pulsatility $\Delta\widetilde{\text{AoP}}$ (h) either a first setup or a second setup.

In the first setup, the control device can be arranged to adjust the speed command signal $n_{VAD}^{set}(t)$ in an open-loop manner, e.g. by a command signal generator. In the first setup, the desired minimum pulsatility $\Delta\widetilde{\text{AoP}}$ (h) can be caused by alternating the speed command signal $n_{VAD}^{set}(t)$ of the VAD between predefined speed levels using an event-based command signal generator.

In the second setup, the control device can be arranged to adjust the speed command signal $n_{VAD}^{set}(t)$ in a closed-loop feedback manner, e.g. by extending a speed control loop for the speed $n_{VAD}(t)$ of the VAD by an additional pressure control loop resulting in a cascade control strategy. In the second setup, the speed command signal $n_{VAD}^{set}(t)$ may be automatically set in the speed command signal generator, e.g. by an outer loop with a feedback pressure control strategy, so that the desired minimum pulsatility $\Delta\widetilde{\text{AoP}}$ (h) can be achieved for the $h^{th}$ heartbeat while taking physiologically induced boundary conditions into consideration. The first setup may also take physiologically induced boundary conditions into consideration.

Such boundary conditions may be e.g. limited available blood volume and/or maximum and/or minimum levels of mean arterial blood pressure $\overline{\text{AoP}}(h)$. For the control device to work within the physiological constraints it may be desirable to monitor the ventricular filling pressures (e.g. with a pressure sensor in the ventricle) or any event of suction, which may occur due to the lack of blood volume (e.g. with a pressure sensor, which is located within or at the VAD inlet to monitor suction-related negative inflow pressures).

The open-loop setup (first setup) and the closed-loop setup (second setup) for the generation of the speed command signal $n_{VAD}^{set}$) may both be configured to operate in an event-based manner, and may both be intended to generate the desired minimum pulsatility $\Delta \widetilde{AoP}$ (h) during the $h^{th}$ heartbeat by adjusting the speed command signal $n_{VAD}^{set}(t)$ of the VAD for the predetermined pulse duration $\tau^{pulse}(h)$.

The control device may consist of an inner control loop for controlling the speed $n_{VAD}(t)$ of the VAD and an outer loop, the structure of which depends on the first or second setup defined above. For the inner (speed) control loop, a common high speed feedback closed-loop control can be used. In the following, the focus will be on the generation of the speed command signal $n_{VAD}^{set}(t)$ of the VAD for the inner control loop.

Preferably, the control device is configured to synchronize the adjustment of the speed command signal $n_{VAD}^{set}$), such as the beginning and/or the end of a command signal pulse, with the heartbeat by using at least one sequence of trigger signals $\sigma(t)$ that is related to at least one predetermined characteristic event in the cardiac cycle.

For example, the control device may be configured to adjust the speed command signal $n_{VAD}^{set}(t)$ so that the blood pressure in the artery of interest produced by the VAD is increased for a predefined time interval of the cardiac cycle. In general, the control device may be configured to set the speed command signal $n_{VAD}^{set}(t)$ for adjusting the VAD speed at a high level during systole and/or at a low level during diastole.

For example, the desired minimum pulsatility may be generated by speed alteration during the systole of the assisted heart only. That is to say, the speed command signal $n_{VAD}^{set}(t)$, which defines the target speed level, may be adjusted by increasing a basic speed level $n_{VAD}^{set}(t) = n_{VAD}^{set,basic}(h)$ to a target speed level $n_{VAD}^{set}(t) = n_{VAD}^{set,basic}(h) + \Delta n_{VAD}^{set}(h)$ before, at or slightly after the beginning of the systole of the assisted heart, and may be reduced again to the basic speed level $n_{VAD}^{set,basic}(h)$ before, at or slightly after the end of the systole. In this way, the increase of the basic speed level $n_{VAD}^{set,basic}(h)$ by adding a speed difference $\Delta n_{VAD}^{set}(h)$ generates a positive speed pulse during the systole of the assisted heart.

Correspondingly, the desired minimum pulsatility may be generated by speed alteration during the diastole of the assisted heart only. That is to say, the speed command signal $n_{VAD}^{set}(t)$ may be adjusted by decreasing the speed level from the basic speed level $n_{VAD}^{set,basic}(h)$ to the target speed level $n_{VAD}^{set}(t) = n_{VAD}^{set,basic}(h) - \Delta n_{VAD}^{set}(h)$ before, at or slightly after the beginning of the diastole of the assisted heart, and may be increasing the speed level to the basic speed level $n_{VAD}^{set,basic}(h)$ again before, at or slightly after the end of the diastole. In this way, the decrease of the basic speed level $n_{VAD}^{set,basic}$) by subtracting a speed difference $\Delta n_{VAD}^{set}(h)$ generates a negative speed pulse during the diastole of the assisted heart.

However, speed command signal alteration during the systolic phase or the diastolic phase is respectively one generic example of synchronization of the speed variation with the heartbeat. It will be appreciated that the desired minimum pulsatility $\Delta \widetilde{AoP}$ (h) may be generated by a combination of both a positive speed pulse during systole and a negative speed pulse during diastole.

Note that the reason for the speed command signal alteration to be synchronized with the cardiac cycle is to enhance the residual pulsatility of the weakened heart, which is due to the native heart contraction in systole. Preferably, the speed command signal alteration results in systolic flow contribution to the native ejection of the heart alone; i.e. a co-ejection of the heart and the VAD is desirable.

Thus, in the first embodiment, restoration and/or maintenance of the desired minimum pulsatility can be achieved by the control device being configured to alter the speed command signal $n_{VAD}^{set}(t)$ for adjusting the speed of the VAD so that the VAD-induced blood flow QVAD(t) is reduced substantially during the diastole of the cardiac cycle and/or is increased substantially during the systole of the cardiac cycle. Thus, the desired minimum pulsatility of the arterial blood pressure can be restored and maintained. The diastolic speed reduction of the VAD may allow the ventricle to fill adequately, so that a systolic co-ejection of blood volume from the VAD and the native heart is possible.

The inventors have found that, as an aim for the speed command signal alteration, the native heart and the VAD both preferably provide adequate systolic peak flow rates so that the total peak flow per heartbeat $$Q_{total|max}(h) = Q_{heart|max}(h) + Q_{VAD|max}(h)$$

and the total ejected volume (EV) per heartbeat $$EV(h) = EV_{heart}(h) + EV_{VAD}(h)$$

result in an adequate increase in systolic systemic blood pressure. The native heart's ability to co-eject may depend on the ventricular preload, on the ventricular filling level, and on the level of heart contractility as well as on the achievable peak flow of the VAD. The native heart's ability to co-eject may also depend on the patient's body mass index, or body surface, or the vascular compliance as well as the peripheral resistance.

For example, a generic patient with a height of 1.75 m and a weight of 75 kg has approximately a mean blood flow of 5 L/min. The demand can be estimated based on a person's body surface area (BSA). The generic patient has a body surface area of about 1.9 m² (based on the formula by R. D. Mosteller, "Simplified calculation of body-surface area", N. Engl. J. Med. 317. No. 17, October 1987, p. 1098). The normal blood flow normalized to the BSA equals approximately 2.6 L/m². A mean blood flow of 5 L/min in a healthy patient at rest results in a blood pressure of about 120 mmHg to 80 mmHg.

A total peak flow $Q_{total|max}(h)$ of about 8 L/min during systole is considered sufficient to result in a desired minimum pulsatility $\Delta \widetilde{AoP}$ (h) of about 15 mmHg in a normal-sized person (BSA 1.9 m²). Thus, more generally, a total peak flow of 8 L/min divided by 1.9 m² and multiplied by the patient's actual BSA may result in a more patient-adapted value of peak flow. As another example, a patient with BSA=1.6 m² may have an equal desired minimum pulsatility $\Delta \widetilde{AoP}$ (h) with just $Q_{total|max}(h) = 6.7$ L/min total peak flow during systole. Taking into account all the variability in compliance and peripheral resistance more generally, a total peak flow between 6 L/min and 10 L/min should be sufficient for the vast majority of patients treated with an assist device to gain a target desired minimum pulsatility of at least $\Delta \widetilde{AoP}$ (h)≥15 mmHg. Accordingly, systolic peak flow rates resulting in a total peak flow of $$Q_{total|max}(h) = Q_{heart|max}(h) + Q_{VAD|max}(h) > 6 \text{ L/min} \ldots$$
$$10 \text{ L/min}$$

which result in total ejected volumes of $$EV(h) = EV_{heart}(h) + EV_{VAD}(h) = 40 \text{ ml} \ldots 70 \text{ ml}$$

are desired so that the desired minimum pulsatility $\Delta \widehat{AoP}$ (h) > [15 . . . 30] mmHg can be achieved.

The desired minimum pulsatility $\Delta \widehat{AoP}$ (h) will not be a fixed value, but may vary based on the recruitment of vWF. Simulation results have underlined the fact that the command signal generator or the outer pressure control loop can either focus on increased pulsatility while accepting reduced mean aortic pressure or focus on increased mean aortic pressure while accepting reduced pulsatility.

The duration of systole at normal heart rate HR≈70 bpm (beats per minute) in humans is normally about $\tau^{Systole}$(h)= 300 ms and varies only marginally with heart rate. Patients in a state of shock are commonly characterized, inter alia, by a heart rate of up to HR≤120 bpm. Thus, a minimum duration of a cardiac cycle is assumed at $\tau$(h)=500 ms. Further, in patients with a higher heart rate HR≥120 bpm, a shortened duration of systole is assumed at about $\tau^{Systole}$(h)= 250 ins.

Therefore, the predetermined pulse duration $\tau^{pulse}$(h) of the speed pulse may be in the range of $\tau^{pulse}$(h)=[200 . . . 300] ms, preferably $\tau^{pulse}$(h)=[225 . . . 275] ms, most preferably about $\tau^{pulse}$(h)=250 ms.

Alternatively, the predetermined pulse duration $\tau^{pulse}$(h) of the speed pulse may be in the range of +/−50% or +/−100 ms of the duration of the systole $\tau^{Systole}$(h) of the assisted heart.

Depending on the residual pulsatility in the artery of interest, the pulse duration of the speed pulse may also be adapted to the heart rate, resulting in a time interval $\tau^{assist}$(h), which preferably depends e.g. on the observations of preceding heart rates and the durations of preceding systolic phases.

Additionally or alternatively, the adjustment of the speed command signal $n_{VAD}^{set}$(t) may be synchronized with the appearance of the R wave in an electrocardiogram (ECG) signal of the patient and/or set to a constant repetition rate e.g. in the case of cardiac arrest.

In a possible practical implementation, the VAD, e.g. in the form of a rotational blood pump, may comprise an actuator, for instance a rotational motor, for driving the blood pump, which produces the VAD-induced blood flow QVAD(t). Then, the control device may alter the speed $n_{VAD}$(t) of the VAD by adjusting the speed command signal $n_{VAD}^{set}$(t) to the target speed level for the rotational motor and controlling the speed $n_{VAD}$(t) of the VAD by a feedback closed-loop control. Accordingly, the modification of the pulsatility, i.e. the pulsatility difference $\Delta AoP_{pulse}$(h), may be associated with a corresponding adjustment of the speed command signal $n_{VAD}^{set}$(t), e.g. by a speed difference $\Delta n_{VAD}^{set}$(h), i.e. the speed command signal $n_{VAD}^{set}$(t) of the rotational motor is increased from a basic speed level $n_{VAD}^{set,basic}$(h) by the speed difference $\Delta n_{VAD}^{set}$(h) for generating the desired minimum pulsatility $\Delta \widehat{AoP}$ (h) which is set by the control device. Thus, the control device may be configured to vary the corresponding higher speed command signal $n_{VAD}^{set}$(t)=$n_{VAD}^{set,basic}$(h)+$\Delta n_{VAD}^{set}$(h) to achieve the desired minimum pulsatility $\Delta \widehat{AoP}$ (h).

In general, the speed difference $\Delta n_{VAD}^{set}$(h) may also be negative, e.g. to generate a negative speed pulse.

It is noteworthy that a desired speed difference $\Delta n_{VAD}^{set}$(h) may be determined based on the achieved pulsatility difference $\Delta AoP_{pulse}$(h), which is largely a function of how much blood volume is delivered to the arterial system in a given time unit. It needs to be understood that any arterial blood pressure built-up is the end result of blood volume being ejected during a time unit into the arterial system with its intrinsic compliance and peripheral resistance.

Preferably, the control device is further configured to adjust the speed command signal $n_{VAD}^{set}$(t) also outside the speed alteration interval, e.g. to adjust the basic speed level $n_{VAD}^{set,basic}$(h), so that a predetermined mean arterial blood pressure $\overline{AoP}$(h) is achieved by the VAD or to avoid any backflow into the ventricle via the pump, which is called regurgitant pump flow.

In a further development, the control device, in particular in the second closed-loop setup, may be configured to adjust the speed command signal $n_{VAD}^{set}$(t) both within and outside the speed alteration interval to achieve the desired minimum pulsatility $\Delta \widehat{AoP}$ (h).

In a further development, the control device may additionally be configured to adjust the speed command signal $n_{VAD}^{set}$(t) while taking into consideration the mean arterial blood pressure per heartbeat $\overline{AoP}$(h) as a control constraint.

For example, the control device may be configured to adjust the speed command signal $n_{VAD}^{set}$(t) to avoid a drop of the mean arterial blood pressure $\overline{AoP}$(h) below a predetermined threshold value $\overline{AoP}_{thr}$(h).

Additionally, the control device may be configured to adjust the speed command signal $n_{VAD}^{set}$(t) so that the speed alteration interval (or speed pulse) is started at a predetermined time interval $\tau^{incr}$(h) before a predetermined characteristic event occurs. This means that the speed change may be induced a time interval $\tau^{incr}$(h) before, e.g., an expected or predicted beginning of the ventricular contraction of the assisted heart, which may be the corresponding characteristic event in the cardiac cycle. This may be of particular importance, since the dynamic response of a particular VAD, e.g. a specific pump, may be delayed due to a pump-specific mechanical and/or hydraulic inertia requiring a latency before the desired effect is provided.

For example, the beginning of the heart contraction, which is defined e.g. by the time of mitral valve closure, may be detected based on a corresponding blood pressure signal. For example, if the VAD is configured for left-sided heart assistance the corresponding blood pressure signal may be the left ventricular pressure.

For example, the atrial contraction preceding the ventricular contraction may be detected. Thus, the event occurs earlier then the event of systolic contraction, allowing the pump to speed up when the beginning of atrial contraction is used as the event.

Alternatively or additionally, the predetermined event may be the occurrence of the R-wave in an ECG signal of the assisted heart.

The time interval $\tau^{incr}$(h) may be useful for taking account of the fact that the speed increase of the VAD is slowed down by hydraulic impacts of the blood on the drive of the VAD. Hence, to increase the speed, the speed command signal $n_{VAD}^{set}$(t) should be increased by a smooth trajectory to avoid hemolysis or other undesired hemodynamic side effects, such as suction or VAD-induced cavitation, when blood would be accelerated too fast.

Additionally, the control device may be configured to end the pulse of the speed command signal $n_{VAD}^{set}$(t) after the predetermined pulse duration $\tau^{pulse}$(h).

Alternatively, the control device may be configured to end the pulse of the speed command signal $n_{VAD}^{set}$(t) after a heart rate dependent pulse duration $\tau^{assist}$(h), i.e., a pulse duration that is adapted by the control device to the heart rate HR(h). In particular, the control device may be configured to end the pulse of the speed command signal $n_{VAD}^{set}$(t) when at least one predetermined characteristic event of the cardiac cycle occurs.

Additionally, the control device may be configured to end the pulse of the speed command signal $n_{VAD}^{set}$) a predetermined time interval $\tau_{red}(h)$ before or when at least one predetermined characteristic event of the cardiac cycle occurs.

For example, the predetermined characteristic event may be the beginning of the relaxation of the assisted heart and/or the closing of the aortic valve.

For example, at least one event may be the beginning of relaxation of the assisted heart. Accordingly, the control device may be configured to derive the occurrence of an event based on a signal that comprises information about characteristic events such as the beginning of relaxation. As a result, the pulse of the speed command signal $n_{VAD}^{set}(t)$ can be synchronized e.g. with the time of occurrence of the maximum drop in pressure within the ventricle of the assisted heart. Note that the time of maximum drop in pressure marks the beginning of ventricular relaxation (relaxation moment) after the preceding systole.

Alternatively or additionally, the control device may be configured to derive the occurrence of at least one event per cardiac cycle based on at least one internal signal of the control device. "Internal signal" of the control device means herein that the signal is a signal which is already internally available to the control device for analysis, such as a control signal provided by the control device to the VAD.

For example, the at least one internal signal may be an electrical current provided to actuate the VAD, such as a motor current supplied to the VAD. Thus, the control device may be configured to derive the occurrence of at least one event per cardiac cycle based on the analysis of the electrical current signal and/or a processed version thereof, for example a time derivative, e.g. the first time derivative.

For example, the VAD may be the above-mentioned rotational blood pump. The blood pump may comprise an actuator, such as a rotational electrical motor, for driving a rotational thrust element, such as an impeller, for producing a corresponding blood flow. In operation of the blood pump, a motor current is consumed by the motor in order to achieve a respective target speed level, according to the set speed command signal $n_{VAD}^{set}(t)$, of the motor and the rotational thrust element. The required motor current $I_{VAD}(t)$ for achieving the target speed depends on the current blood pressure difference $\Delta p(t)$ the blood pump needs to overcome, such as the difference between the blood pressures within the aorta AoP(t) and within the left ventricle LVP(t), $$\Delta p(t)=AoP(t)-LVP(t).$$

In other words, the electrical current supplied to the blood pump corresponds directly to the electrical current required by the motor of the blood pump to achieve the set speed $$I_{VAD}(t)=f(n_{VAD}^{set}(t),\Delta p(t)).$$

Thus, the motor current supplied to the VAD by the control device or by a supply unit controlled by the control device can be used as an internal signal to derive the occurrence of at least one event per cardiac cycle.

Furthermore, the control device may be further configured to estimate the current VAD-induced blood flow $Q_{VAD}(t)$, which is based on the electrical current signal and on known calculation specifications with a pump characteristic correlation between motor current at a given speed, pump flow and pressure difference.

Alternatively or additionally, the control device may be configured to derive the occurrence of at least one event per cardiac cycle from at least one external signal provided to the control device. "External signal" means herein that the signal is a signal which is received by the control device from external sensors such as one or more blood pressure sensors of the VAD and/or from external devices such as a patient monitoring unit or an electrocardiograph (ECG). Such external signals can be fed into the control device via corresponding interfaces or input terminals, to be available in the control device for processing and/or analysis by the control device.

For example, the measuring signal may represent at least one of a blood pressure difference $\Delta p(t)$ between an outlet of the VAD and an inlet of the VAD, a blood pressure in a ventricle of the assisted heart LVP(t), a blood pressure in the aorta AoP(t) adjacent to the assisted heart, a blood pressure in the vena cava CVP(t) adjacent to the assisted heart, a blood pressure in the pulmonary artery PAP(t) adjacent to the assisted heart, just to give some examples. The waveforms of all of these measuring signals may contain information descriptive of the time of occurrence of particular characteristic events in the cardiac cycle.

For example, if the VAD is the above-discussed rotational blood pump, it may comprise an inlet for sucking in blood from the heart, e.g. from the inside of a ventricle, and an outlet for ejecting blood to a vessel adjacent to the heart, such as the artery of interest, which may be the aorta or pulmonary artery depending on whether the VAD is inserted to the left side or the right side of the heart.

For example, as published e.g. in U.S. Pat. No. 5,911,685 A, the VAD may comprise at least one of a pressure sensor for measuring the blood pressure at the inlet of the VAD, such as a ventricular pressure in the assisted heart, and a pressure sensor for measuring the blood pressure in a vessel adjacent to the heart, such as the blood pressure in the aorta or pulmonary artery adjacent to the assisted heart. Alternatively or additionally, the VAD may comprise one differential pressure sensor for measuring the differential blood pressure between the outlet and the inlet of the VAD.

Additionally, the control device may be configured to receive, store and analyze at least one measuring signal which contains information about characteristic points of the cardiac cycle, and which can be used to estimate the current working phase of the heart in the cardiac cycle. Then, the control device may be configured to predict the time of re-occurrence of a particular characteristic during the next cardiac cycle based on information about previous cardiac cycles.

Basically, in all embodiments, the at least one measuring signal may be at least one of an ECG signal, a measuring signal representing the blood pressure in the left ventricle or the right ventricle of the heart, a measuring signal of the blood pressure in the vena cava or the aorta or in the pulmonary artery adjacent to the heart.

Thus, for predicting the next time of occurrence of at least one event based on information on previous cardiac cycles, the chosen signal may preferably contain information about the cardiac cycle, so that the time of occurrence of at least one event per cardiac cycle can be predicted based on the chosen measurement signal and on detected events during previous cardiac cycles.

Additionally or alternatively, the control device may be configured to eliminate the effect of active heart assistance by the VAD on the measuring signals from said measuring signals. In particular, the control device may be configured to analyze at least two, preferably independent, measuring signals by data fusion with the aim of detecting the predetermined events in a cardiac cycle despite the effect of the VAD-induced pressure change on the cardiac dynamic behavior.

In particular embodiments, the control device may be configured to set the speed of the VAD so that in the diastolic phase of the cardiac cycle of the assisted heart the amount of blood ejected by the VAD into the artery of interest, such as the aorta or the pulmonary artery, is low enough such that a blood volume remains in the corresponding ventricle and the co-ejection of the VAD and the ventricle during systole results in a preferred minimum peak blood flow, i.e. the minimum peak blood flow is preferably about 6 L/min, more preferably 7 L/min, most preferably 8 L/min and more (as discussed above).

The systolic peak flow will largely depend on the native heart's ability to co-eject, depending specifically on the ventricular preload, the ventricular filling level, and the level of heart contractility as well as the achievable peak flow of the VAD. The total peak flow per heartbeat $Q^{total|max}(h)$ and the total ejected volume per heartbeat $EV(h)$ will need to result in an adequate increase in systolic systemic blood pressure, as described above. This, however, also depends on the patient's body mass index, or body surface, the vascular compliance as well as peripheral resistance. In other words, a minimum total peak flow of $Q^{total|max}(h)=6$ L/min may be sufficient in a small patient, but a higher total peak flow may be required in a larger patient (as discussed above). A higher total peak flow may especially be required if the vascular bed is relaxed or wide open.

Additionally, the control device may be configured to adjust the speed command signal $n_{VAD}^{set}(t)$ in the form of a pulse during the cardiac cycle only if the resulting mean arterial blood pressure per heartbeat $\overline{AoP}(h)$ does not drop below a predetermined threshold value $\overline{AoP}_{thr}(h)$.

The minimum VAD-induced blood flow $Q_{VAD}(h)$ may correspond to a required minimum heart assistance to be provided by the VAD to a weakened heart. The idea is that the VAD can be operated so as both to obtain the desired recruitment of vWF and to ensure that a required minimum blood flow is provided. For example, currently required blood flow may be related to a patient's current perfusion demand, taking into consideration periods of required high assistance, e.g. daytime activity, walking, climbing stairs, and so on, in which case the VAD will run at relatively high mean speeds. Periods of low patient perfusion demands. e.g. at rest, while sleeping, etc., can be used to run the VAD at lower mean speeds. This will help to increase pulsatility and assist the recruitment of vWF while still maintaining some degree of blood flow support. Of course a more sophisticated regime is possible in which the current demand for heart assistance corresponding to a particular, e.g. average, VAD-induced blood flow $Q_{VAD}(h)$ is taken into consideration in a continuous manner. Thus, the control device may be configured to use any available surplus between a currently required minimum blood flow and the maximum blood flow that the VAD may provide for the restoration and maintenance of a residual pulsatility as proposed here.

It is noted that it can further be advisable to synchronize the alteration of the speed in a "y in x" manner, i.e. the proposed speed pulse is generated only in y out of x consecutive cardiac cycles. For example, a speed pulse aiming to restore or maintain a desired minimum pulsatility may be induced in a one in two or one in three or one in four manner or in a two in three or two in four or two in five manner, i.e. in one cardiac cycle in every two or in every three or in every four consecutive cardiac cycles and in two cardiac cycles in every three or in every four or in every five consecutive cardiac cycles, respectively. This may be particular beneficial if the heart frequency is too high or if the level of pump assistance for the heart is not adequate. Thus, an augmented pulsatility is only provided intermittently. It has been found that this can serve the purpose of vWF recruitment perfectly. For example, the control device can additionally be configured to set the speed $n_{VAD}(t)$ of the VAD, during at least y of the other (x-y) consecutive cardiac cycles of the assisted heart so that the mean arterial blood pressure per heartbeat remains above the predetermined threshold value ($\overline{AoP}(h) \geq \overline{AoP}_{thr}(h)$).

Finally, the above-discussed functions or functionalities of the control device can be implemented by a corresponding computing unit, in hardware or software or any combination thereof, of the control device. Such computing unit can be configured by means of corresponding computer programs with software code for causing the computing unit to perform the respectively required control steps. Such a programmable computing unit is well known in the art and to the person skilled in the art and therefore need not be described here in detail. Moreover, the computing unit may comprise particular dedicated hardware useful for particular functions, such as one or more signal processors for processing and/or analyzing e.g. the discussed measuring signals. Further, respective units for controlling the speed of a drive of the VAD may be implemented by respective software modules as well.

The corresponding computer programs can be stored on a data carrier containing the computer program. Alternatively, the computer program may be transferred, e.g. via the Internet, in the form of a data stream comprising the computer program without the need of a data carrier.

A second aspect of the invention provides a VAD comprising one of the control devices according to the first aspect of the invention. For example, the VAD may be a rotational blood pump, i.e. a blood pump driven by a rotational motor.

For example, such blood pump may be catheter-based to be implanted or placed directly into a heart via corresponding blood vessels.

For example, the VAD may be a blood pump as published e.g. in U.S. Pat. No. 5,911,685, which is particularly arranged for a temporary placement or implantation into the left or right heart of a patient.

Preferably, the VAD is a low inertia device by comprising, but not being limited to, one or more of the following characteristics: (1) moving, in particular rotating, parts, for example a rotor or impeller, of the VAD may comprise low masses by being made of a low weight material, such as plastic materials, synthetic materials or the like; (2) a driving means, such as an electric motor, may be arranged near, preferably very near, most preferably adjacent, to a part, for example a rotor or impeller, driven by the motor, and, if catheter-based, should preferably not include any rotational drive cable or drive wire, but electric wiring; (3) a coupling or connection, for example a shaft, of the motor with a part, for example a rotor or impeller, driven by the motor may be made short; (4) all moving parts, in particular rotating parts, of the VAD may have small diameters. Note that the foregoing list of characteristics does not claim to be complete, i.e. the device may comprise further or alternative characteristics that make the device a low inertia device.

BRIEF DESCRIPTION OF THE DRAWINGS

Hereinafter the invention will be explained by way of examples with reference to the accompanying drawings; in which.

DETAILED DESCRIPTION

Figure 1:
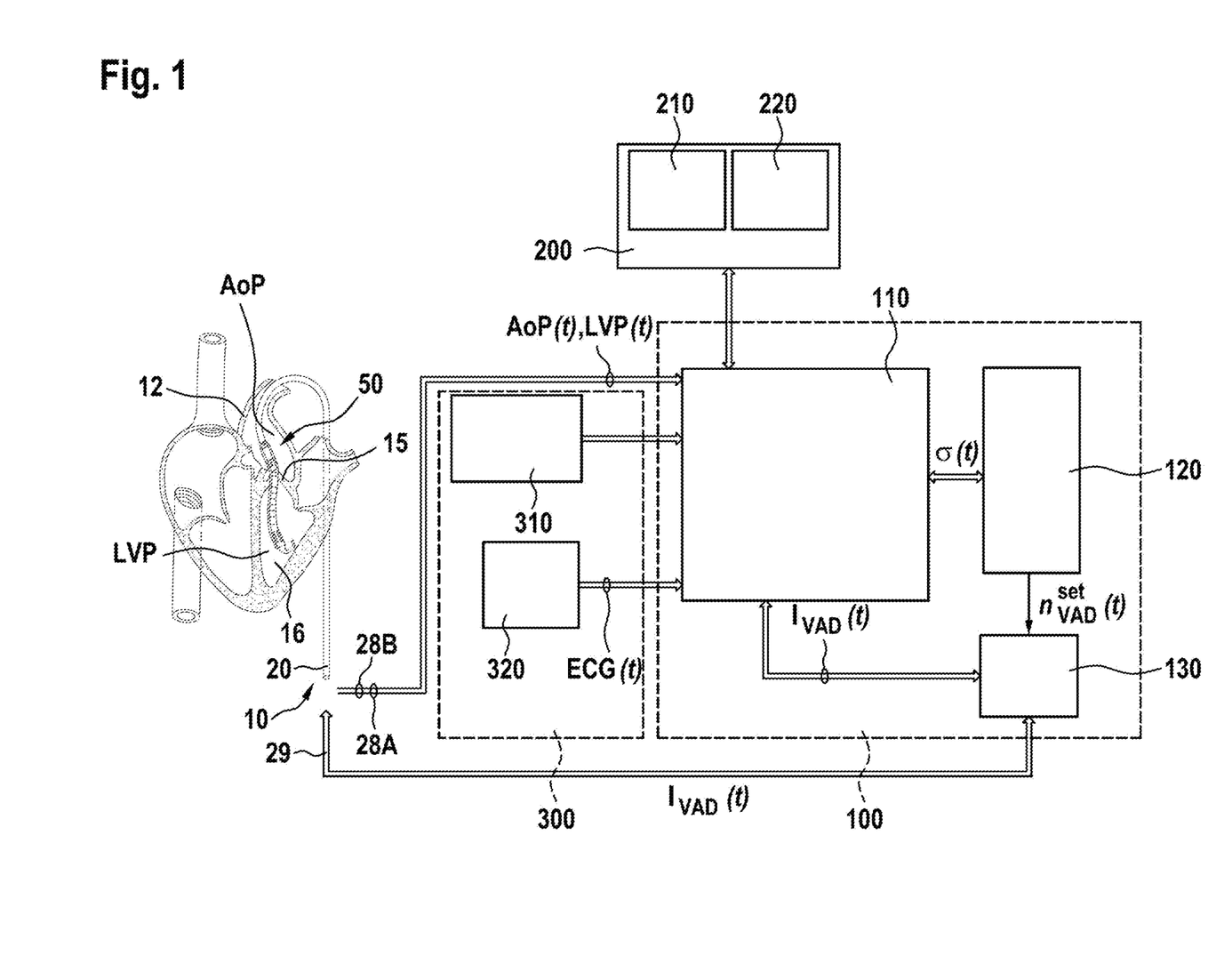
FIG. 1 shows one exemplary embodiment of a VAD placed through the aorta and extending through the aortic valve into the left ventricle of a heart, and a block diagram of an exemplary embodiment of the control device for the VAD.

FIG. 1 shows a catheter-based rotational blood pump (in the following called "blood pump") on the left hand side, which is described herein as one exemplary embodiment of a VAD. This exemplary blood pump is shown in more detail in FIG. 2.

As noted above, one important physical prerequisite which was found by the inventors to be fulfilled by the VAD to be used for the applications proposed herein is the absence of any relevant inertia. The rotary blood pumps such as a blood pump of the catheter-based pump type shown in FIG. 2 do not have any relevant inertia which would hinder the implementation of the proposed speed control scenarios with within-a-beat speed modulation.

The blood pump is based on a catheter 10 (catheter-based blood pump), by means of which the blood pump is temporarily introduced through the aorta 12 and the aortic valve 15 into the left ventricle 16 of a heart. As shown in more detail in FIG. 2, the blood pump comprises in addition to the catheter 10 a rotary pumping device 50 fastened to the end of a catheter tube 20. The rotary pumping device 50 comprises a motor section 51 and a pump section 52 located at an axial distance therefrom. A flow cannula 53 is connected to the pump section 52 at its one end, extends from the pump section 52 and has an inflow cage 54 located at its other end. The inflow cage 54 has attached thereto a soft and flexible tip 55. The pump section 52 comprises a pump housing with outlet openings 56. Further, the pumping device 50 comprises a drive shaft 57 protruding from the motor section 51 into the pump housing of the pump section 52. The drive shaft 57 drives an impeller 58 as a thrust element by means of which, during operation of the blood pump, blood can be sucked through the inflow cage 54 and discharged through the outlet openings 56.

The pumping device 50 can also pump in the reverse direction when adapted accordingly, e.g. as required when the blood pump is placed in the right heart. In this regard and for the sake of completeness, FIG. 1 shows the rotary blood pump as one particular example of a VAD located in and for assistance of the left heart. For assistance of the right heart, the rotary blood pump of the present example may be temporarily introduced into the right heart from the vena cava and located in the right heart so that blood can be ejected into the pulmonary artery. In this configuration, the blood pump may be configured for sucking in blood from the vena cava or from the right ventricle and for ejecting the blood into the pulmonary artery. That is to say, the principles and functionalities described by the one particular embodiment may be transferred correspondingly for right-sided heart assistance. Thus, no detailed description is required.

Figure 2:
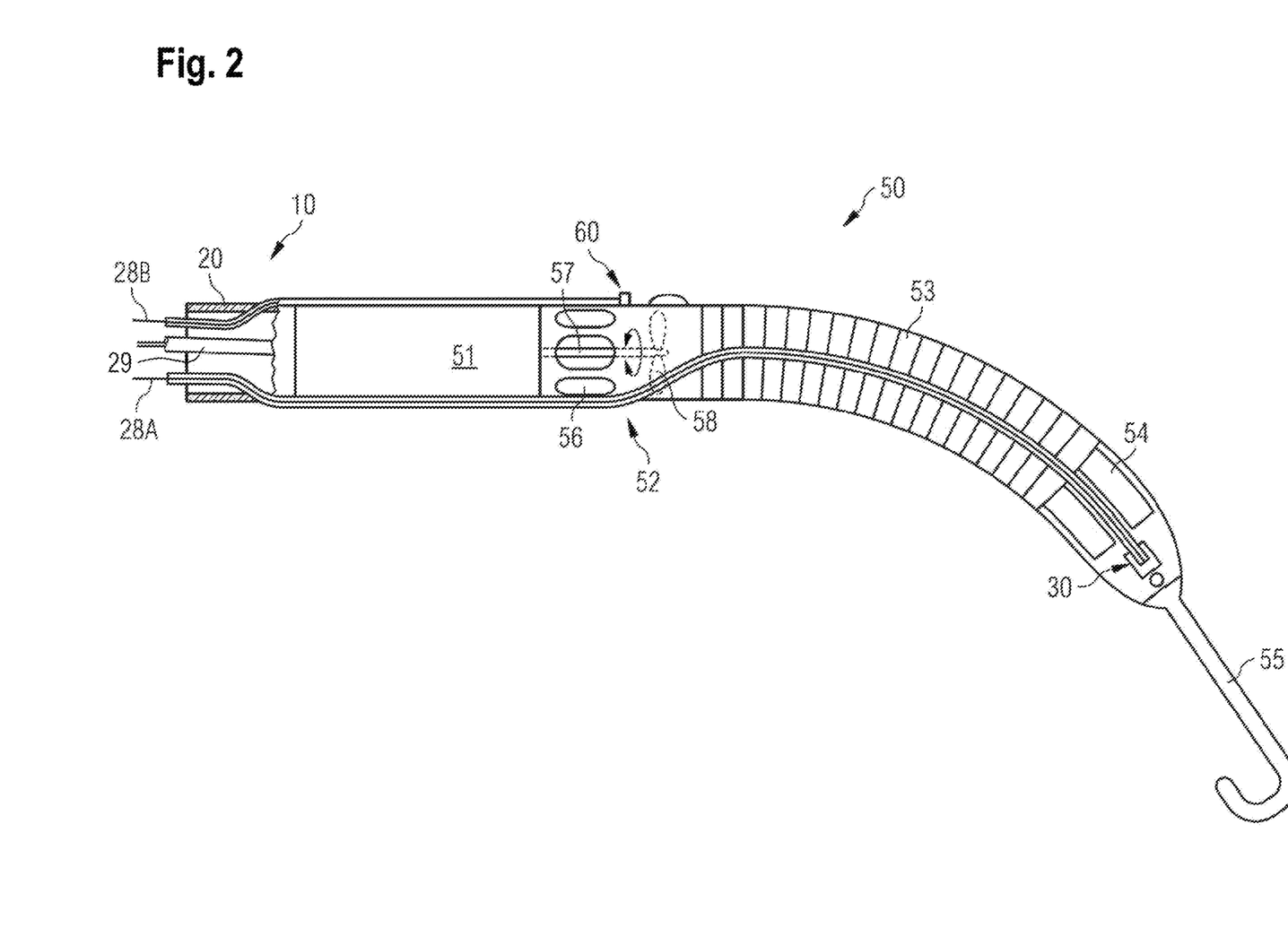
FIG. 2 shows a side view of the exemplary VAD of FIG. 1 in more detail.

In FIGS. 1 and 2, three lines, two signal lines 28A and 28B and a power-supply line 29 for suppling an electrical current to the motor section 51, pass through the catheter tube 20 of the catheter 10 to the pumping device 50. The two signal lines 28A, 28B and the power-supply line 29 are attached at their proximal end to a control device 100. It goes without saying that there may be additional lines for further functions; for example, a line for a purge fluid (not shown) may pass through the catheter tube 20 of the catheter 10 to the pumping device 50 as well. Additional lines may be added based on different sensing technologies.

As shown in FIG. 2, the signal lines 28A, 28B are parts of blood pressure sensors with corresponding sensor heads 30 and 60, respectively, which are located externally on the housing of the pump section 52. The sensor head 60 of the first pressure sensor is associated with signal line 28B. The signal line 28A is associated with and connected to the sensor head 30 of the second blood pressure sensor. The blood pressure sensors may, for example, be optical pressure sensors functioning according to the Fabry-Perot principle as described in U.S. Pat. No. 5,911,685 A, in which case the two signal lines 28A, 28B are optical fibers. However, other pressure sensors may be used instead. Basically, signals of the pressure sensors, which carry the respective information on the pressure at the location of the sensor and which may be of any suitable physical origin, e.g. of optical, hydraulic or electrical, etc., origin, are transmitted via the respective signal lines 28A, 28B to corresponding inputs of a data processing unit 110 of the control device 100. In the example shown in FIG. 1, the pressure sensors are arranged so that the aortic pressure AoP(t) is measured by sensor head 60 and the left ventricular pressure LVP(t) is measured by sensor head 30.

The data processing unit 110 is configured for acquisition of all external and internal signals, for actual signal processing, which includes for example calculation of a difference between two pressure signals as a basis for estimating pump flow, for signal analysis to detect characteristic events during the cardiac cycle based on the acquired and calculated signals, and for generating a sequence of trigger signals σ(t) by means of a trigger signal generator, for triggering a speed command signal generator 120 (see details below).

The data processing unit 110 is connected via corresponding signal lines to additional measurement devices 300, such as a patient monitoring unit 310 and an electrocardiograph 320; these devices are just two examples, i.e. other measuring devices may provide useful signals and therefore be used as well. The electrocardiograph 320 provides an ECG signal ECG(t) to the data processing unit 110.

The control device 100 further comprises a user interface 200 comprising a display 210 and a communication interface 220. On the display 210, setting parameters, monitored parameters, such as measured pressure signals, and other information is displayed. Further, by means of the communication interface 220, the user of the control device 100 can communicate with the control device 100, e.g. to change settings of the whole system.

The data processing unit 110 is particularly configured to derive or predict the time of occurrence of one or more predefined characteristic events during the cardiac cycle of the assisted heart by means of real-time analysis of current signal values which are used for generation of a sequence of trigger signals σ(t) by means of a trigger signal generator. The resulting sequence of trigger signals σ(t) is forwarded to the speed command signal generator 120 to trigger speed command signal changes.

Further, the data processing unit 110 is configured to analyze previous values of these speed command signals $n_{VAD}^{set}(t)$, as well. That is, the data processing unit 110 is also configured to predict the time of occurrence of the at least one predefined characteristic event in the upcoming cardiac cycle based on the stored information about the characteristic events occurring during the current and/or previous cardiac cycles.

One particular characteristic event of the cardiac cycle may be the beginning of contraction of the heart at the beginning of the systolic phase. The detected occurrence or the predicted occurrence of such characteristic event is used as an event for synchronizing the pulse of the speed command signal $n_{VAD}^{set}(t)$ as proposed herein with the cardiac cycle.

The speed command signal generator 120 is configured to generate and adjust the speed command signal $n_{VAD}^{set}(t)$ of the pumping device 50 and to provide it to a speed control unit 130 either in a feedforward setup as an event-based command signal generator (first setup) or in an outer feedback closed-loop setup for pressure control (second setup).

In the first setup, the speed command signal generator 120 is triggered by at least one sequence of trigger signals σ(t) which is provided by the data processing unit 110. In the second setup, the speed command signal $n_{VAD}^{set}(t)$ is provided by a pressure control algorithm (as the command signal generator 120) which operates in an outer feedback loop and is fed with external and internal signals by the data processing unit 110, and triggered by at least one sequence of trigger signals σ(t) provided by the data processing unit 110 to achieve the desired minimum pulsatility $\Delta \widetilde{AoP}(h)$.

Accordingly, the speed control unit 130 controls the speed $n_{VAD}(t)$ of the VAD, in accordance with the speed command signal $n_{VAD}^{set}(t)$, by supplying a motor current $I_{VAD}(t)$ to the motor section 51 of the pumping device 50 via the power-supply line 29 that leads through the catheter tube 20. The current level of the supplied motor current $I_{VAD}(t)$ corresponds to the electrical current currently required by the pumping device 50 to establish the target speed level as defined by the speed command signal $n_{VAD}^{set}(t)$. Via the power-supply line 29, the pump also communicates with the control unit 100.

A measuring signal such as the supplied motor current $I_{VAD}(i)$ which is used as a representative signal of an internal signal of the control device 100 is provided to the data processing unit 110 for further processing.

According to the first aspect of the present invention, the control device 100 is configured for altering the speed of the blood pump of FIGS. 1 and 2 as an exemplary embodiment of a VAD for heart assistance.

The control device 100 is particularly configured to alter the speed of the blood pump 50 within a cardiac cycle of the assisted heart, resulting in a change of the blood flow through the pump, the speed alteration of which is synchronized with the heartbeat by means of at least one event per cardiac cycle which is related to a predetermined event in the cardiac cycle. That is to say, the speed command signal generator 120 may be triggered by at least one sequence of trigger signals σ(t) provided by the trigger signal generator of the data processing unit 110 which obtains information on at least one particular event in the cardiac cycle the occurrence of which is detected, the corresponding signal information being used to set the sequence of trigger signals σ(t).

But it should be noted that the trigger signal generator which provides the sequence of trigger signals σ(t) may rely on more than one event in the cardiac cycle to be detected during each cardiac cycle and to be analyzed to derive a corresponding sequence of trigger signals σ(t) for adjusting the command signal $n_{VAD}^{set}(t)$ and, thus, for altering the speed $n_{VAD}(t)$ of the blood pump 50.

As discussed above, the blood pump comprises the rotary pumping device 50, with the (rotational) speed $n_{VAD}(t)$ of the impeller being controlled by speed control unit 130. The speed command signal $n_{VAD}^{set}(t)$ of the blood pump is adjusted by the command signal generator 120.

According to a first embodiment of the proposed change of blood flow produced by the blood pump, the control device 100, in particular the speed command signal generator 120, is configured to adjust the speed command signal $n_{VAD}^{set}(t)$ of the rotary pumping device 50 so that the resulting speed $n_{VAD}(t)$ of the VAD is altered to generate a VAD-induced blood flow $Q_{VAD}(t)$, which induces a pressure pulse within each cardiac cycle.

For a better understanding, an example of the potential effect of the speed alteration is illustrated in FIG. 3. FIG. 3 shows a diagram with exemplary waveforms.

The waveforms in FIG. 3a) represent the aortic pressure signal distinguishing between physiological (non-assisted) aortic pressure AoP(t) (dashed line) and desired (assisted) aortic pressure $\widetilde{AoP}(t)$ (solid line).

The waveform in FIG. 3b) represents the signal for the left ventricular pressure LVP(t) with examples for characteristic pressure values and/or events in the cardiac cycle which may be used for generating or deriving a sequence of trigger signals σ(t).

The waveform in FIG. 3c) represents an ECG signal.

The diagram of FIG. 3 illustrates by way of one example the principle of a pulsatile blood pressure restoration and maintenance using the blood pump of FIGS. 1 and 2 under control of the control device 100 in FIG. 1.

To this end, FIG. 3d) shows one particular example of a speed command signal $n_{VAD}^{set}(t)$.

In FIG. 3e), a corresponding sequence of trigger signals σ(t) is illustrated.

The speed command signal $n_{VAD}^{set}(t)$ is used for the pump speed alteration which corresponds to the signal output of the speed command signal generator 120, and which is forwarded to the speed control unit 130. The sequence of trigger signals σ(t) is the basis for the event-based speed command signal generation or the event-based closed-loop pressure control resulting in an altered speed command signal $n_{VAD}^{set}(t)$, the alteration of which is synchronized with the heartbeat.

The command signal $n_{VAD}^{set}(t)$ represents a speed increase from a basic speed level $$n_{VAD}^{set}(t) = n_{VAD}^{set,basic}(j)$$

to an increased speed level $$n_{VAD}^{set}(t) = n_{VAD}^{set,basic}(j) + \Delta n_{VAD}^{set}(j)$$

at the beginning of a speed pulse, wherein $\Delta n_{VAD}^{set}(j)$ represents the speed difference during the speed pulse.

In FIG. 3, the beginning of the speed pulse is synchronized with the end of diastole. Further, the speed decrease from the increased speed level $$n_{VAD}^{set}(t) = n_{VAD}^{set,basic}(j) + \Delta n_{VAD}^{set}(j)$$

back to the basic speed level $$n_{VAD}^{set}(t) = n_{VAD}^{set,basic}(j)$$

at the end of the speed pulse is also shown.

In FIG. 3, the end of the speed pulse is synchronized with the end of systole. These speed alterations each represent possible implementations of speed alteration for achieving the desired minimum pulsatility as discussed in the general section herein.

The speed decrease is triggered so that a pulse of the speed command signal $n_{VAD}^{set}(t)$ after a heart rate dependent pulse duration $\tau^{assist}(h)$, i.e., the pulse duration is adapted to the heart rate HR(h). That is to say, the command signal generator 120 is configured to generate a speed pulse with a heart rate dependent pulse duration.

Alternatively, the speed decrease can be triggered so that a predetermined pulse duration $\tau^{pulse}(j)$ is achieved. To this end, the command signal generator 120 can be configured to generate a speed pulse with a predetermined pulse duration $\tau^{pulse}(j)$.

In the shown example (FIG. 3d), the speed increases by the speed difference $\Delta n_{VAD}^{set}(j)$ at the beginning of the speed pulse ends here e.g. at time point $t^{LVP}_{j,ED}$, and the speed decrease at the end of the speed pulse ends here e.g. at time point $t^{AoP}_{j,ES}$.

Preferably, in operation, the speed command signal generator 120 is configured to control pulsatility ΔAoP(h) by adjusting the speed difference $\Delta n_{VAD}^{set}(h)$ accordingly. As discussed above, a desired minimum pulsatility in the range of $\Delta \overline{AoP}$ (h)=[15 . . . 30] mmHg is considered as sufficient so that a deficiency in the vWF may not occur and/or microvascular perfusion may be improved.

Further, as discussed above, the data processing unit 110 is configured to measure and/or calculate the current mean arterial blood pressure per heartbeat $\overline{AoP}(h)$ and to supply the current value to the speed command signal generator 120. To this end, the speed command signal generator 120 is further configured to adjust the speed command signal $n_{VAD}^{set}(t)$ to preferably avoid a drop of the arterial blood pressure below a predetermined threshold value $\overline{AoP}(h) \geq \overline{AoP}_{thr}(h)$.

As discussed in the general section, restoration and/or maintenance of a sufficient minimum blood pressure pulsatility can be achieved by altering the speed of the rotary pumping device 50 so that the VAD-induced blood flow $Q_{VAD}(t)$ is reduced substantially during diastole of the cardiac cycle and/or is increased substantially during systole of the cardiac cycle. Thus, in particular embodiments, the speed command signal generator 120 is configured to adjust the speed command signal $n_{VAD}^{set}(t)$ so that in the diastolic phase of the cardiac cycle of the assisted heart the blood volume ejected to the aorta (or pulmonary artery) is low such that a predetermined volume remains in the left (right) ventricle and the rotary pumping device 50, together with the left (right) ventricle, co-ejects appropriate blood volumes during systole. In other words, the diastolic speed reduction also allows the heart to fill adequately, so that a systolic co-ejection of blood from the rotary pumping device 50 and the native heart is possible. In this regard, the inventors have found that the pump and the native heart should induce a total peak flow during systole of $$Q_{total|max}(h)=Q_{heart|max}(h)+Q_{pump|max}(h)>6 \text{ L/min} \ldots 10 \text{ L/min},$$

resulting in total ejected volumes of $$EV(h)=EV_{heart}(h)+EV_{pump}(h)=40 \ldots 70 \text{ ml},$$

so that the desired minimum pulsatility $\Delta \overline{AoP}$ (h)≥15 . . . 30 mmHg can be achieved. Nevertheless, the targeted desired minimum pulsatility $\Delta \overline{AoP}$ (h) will not be a fixed value, but may vary based on the recruitment of vWF. Moreover, if the native pulsatility of a weakened heart is already higher than the desired minimum pulsatility, then the pulsatility will of course not necessarily be reduced.

The inventors have validated the values stated for peak flows per heartbeat of the pump $Q_{pump|max}(h)$ and the heart $Q_{heart|max}(h)$ and the corresponding total ejection volumes per heartbeat of the pump $EV_{pump}(h)$ and the heart $EV_{heart}(h)$ by means of a mathematical model of an electrical equivalent circuit. The model used is illustrated in FIG. 4.

Figure 4:
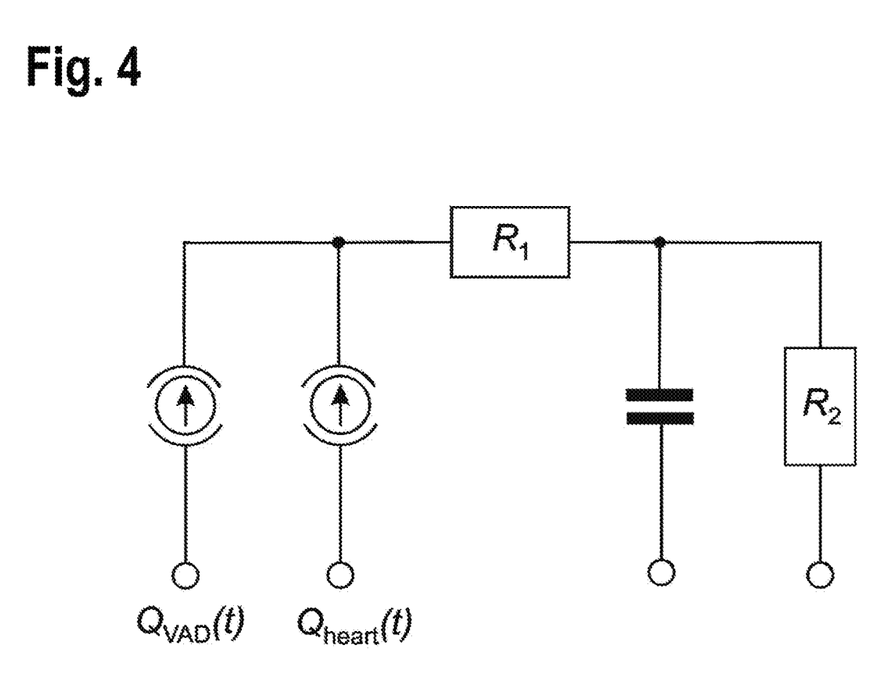
FIG. 4 shows an electrical equivalent circuit of an electrical model approximating the so-called Windkessel effect in the aorta.

FIG. 4 shows the circuit of the electrical model approximating the dynamics of the so-called Windkessel effect in the aorta when blood is ejected by the heart. The electrical model consists of a resistor ($R_1$=0.05 Ohm) representing the resistance of the aortic valve in series with a series connection of another resistor ($R_2$=1.32 Ohm) representing the resistance of the peripheral system of the arteries, and a capacitor ($C_2$=1.7 F) representing the arterial compliance. Further, in the model, the (residual) cardiac output $Q_{heart}(h)$ and the blood flow of the pump $Q_{pump}(h)$ are assumed as current sources. Representing a rotatory blood pump, a standard pump Impella 5.0 was used; for more details, reference is made to Catanho et al., "Model of Aortic Blood Flow Using the Windkessel Effect", Beng 221, Mathematical Methods in Bioengineering, Report, 2012.

Figure 5:
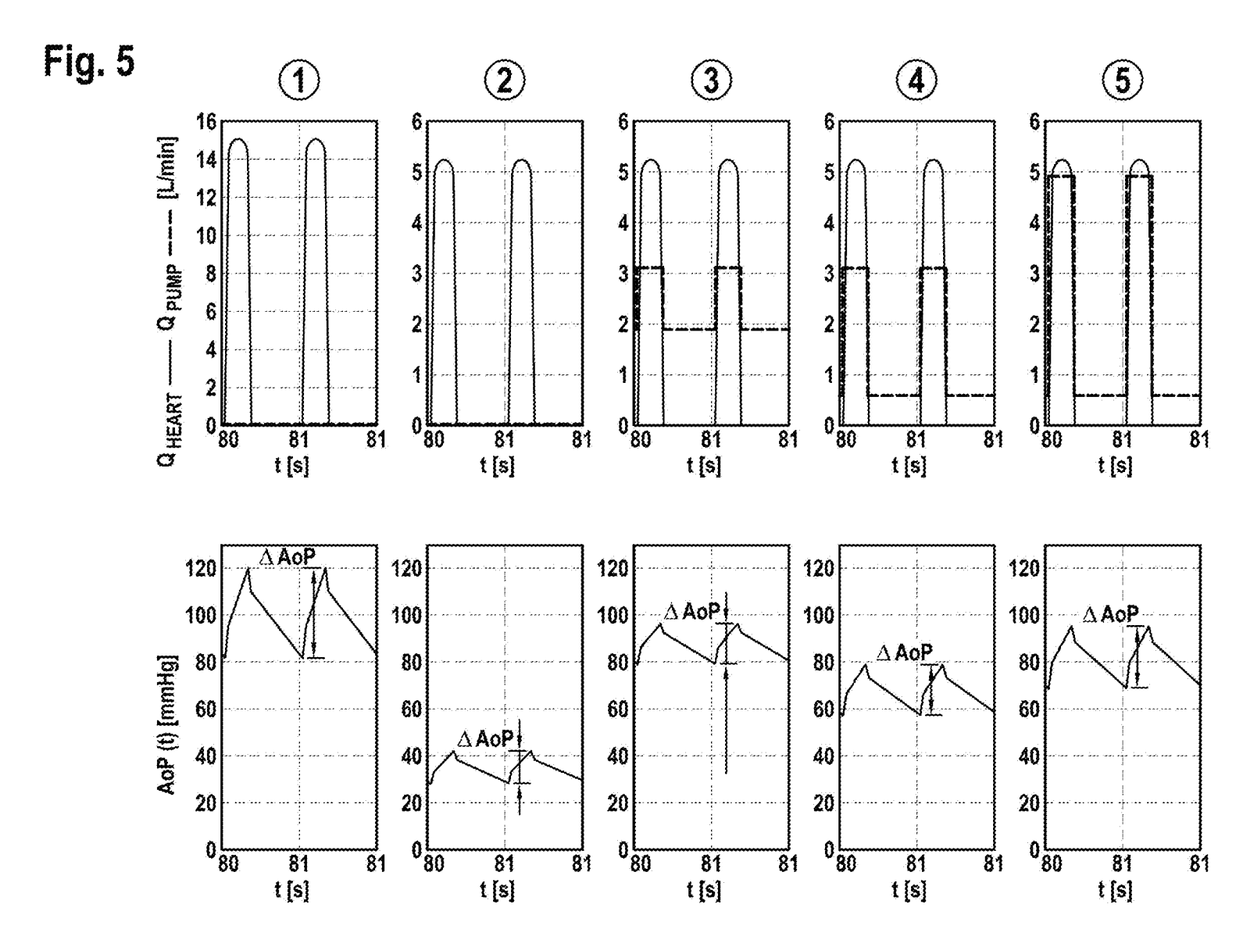
FIG. 5 shows the results of five different simulation scenarios with respect to the blood flow of the heart $Q_{heart}$(t) and blood flow of the pump $Q_{pump}$(t) (upper plots) and aortic pressure AoP(t) (lower plots).

FIG. 5 represents the results of five different simulation scenarios. The table below shows the results of the five different simulation scenarios with additional information on total blood flow for a heartbeat j ($Q_{total}(j)$) and corresponding pulsatility (ΔAoP(j)).

In FIG. 5, from the left to the right, the considered scenarios ① to ⑤ were the following:

Scenario ①—"healthy heart": A native heart function is assumed, resulting in peak flows of the heart $Q_{heart|max}(j)$= 15 L/min and a pulsatility of ΔAoP(j)=40 mmHg (120/80 mmHg) with a common mean aortic blood pressure $\overline{AoP}(j)$=105.4 mmHg.

Scenario ②—"weakened heart, no assistance": The heart function is reduced to a third of the native function, resulting in a peak flow of the heart $Q_{heart|max}(j)$=5.4 L/min and a very low pulsatility of ΔAoP(j)=14.5 mmHg (42/28 mmHg) with an unphysiologically low mean aortic blood pressure of $\overline{AoP}(j)$=36.8 mmHg while no pump is implanted.

Scenario ③—"full unloading (P4)": The weakened heart is assisted by a pump at speed level P4 with the aim of generating maximum flow, resulting in a total peak flow of $Q_{total|max}(V)=Q_{heart|max}(j)+Q_{pump|max}(j)$=8.5 L/min and a moderate pulsatility of ΔAoP(j)=17.2 mmHg (96/79 mmHg) with a physiologically mean aortic blood pressure of AoP (j)=89.8 mmHg.

Scenario ④—"low pulsatility (P4/P2)": The weakened heart is assisted by a pump, the speed of which is altered with the speed of scenario ③ (P4) at systole and low speed (P2) at diastole, resulting in a total peak flow of $Q_{total|max}(j)=Q_{heart|max}(j)+Q_{pump|max}(j)$=8.5 L/min and a higher moderate pulsatility of ΔAoP(j)=20.4 mmHg (78/58 mmHg) compared to scenario ③ at a lower mean aortic pressure of $\overline{AoP}(j)$=70.6 mmHg.

Scenario ⑤—"high pulsatility (P9/P2)": The weakened heart is assisted by a pump, the speed of which is altered with the highest possible speed (P9) at systole and low speed (P2) at diastole, resulting in a high total peak flow of $Q_{total|max}(j)=Q_{heart|max}(j)+Q_{pump|max}(j)$=10.3 L/min and the highest possible pulsatility of ΔAoP(j)=27.4 mmHg (95/69 mmHg) at a moderate mean aortic pressure of $\overline{AoP}(j)$=85.2 mmHg.

It should be noted that in Scenario ③-⑤ it is assumed that the heart ejects the same amount during systole despite varying degrees of diastolic unloading by the pump.

| Values for heartbeat j Scenario | $Q_{heart}\|_{max}$ [L/min] | $Q_{pump}\|_{max}$ [L/min] | $Q_{total}$ [L/min] | $EV_{heart}$ [ml] | $EV_{pump}$ [ml] | $\Delta AoP$ [mmHg] | $\overline{AoP}$ [mmHg] |
|---|---|---|---|---|---|---|---|
| ① "healthy heart" | 15.0 | 0.0 | 4.34 | 72.3 | 0.0 | 40.0 | 105.4 |
| ② "weakened heart, no assistance" | 5.4 | 0.0 | 1.51 | 25.2 | 0.0 | 13.5 | 36.8 |
| ③ "full unloading (P4)" | 5.4 | 3.1 | 3.81 | 25.2 | 38.2 | 17.2 | 89.8 |
| ④ "low pulsatility (P4/P2)" | 5.4 | 3.1 | 2.94 | 25.2 | 23.8 | 20.4 | 70.6 |
| ⑤ "high pulsatility (P9/P2)" | 5.4 | 4.9 | 3.54 | 25.2 | 33.8 | 27.4 | 85.2 |

In summary, the simulation results underline the fact that the speed alteration can either focus on increased pulsatility while accepting reduced mean aortic pressure or focus on increased mean aortic pressure while accepting reduced pulsatility. Physical and physiological constraints were taken into consideration here, such as very low inertia and hemolysis.

In particular, the data processing unit 110 is configured to trigger the speed command signal generator 120 so that the pulse of the speed command signal $n_{VAD}^{set}(t)$ begins and/or ends at the detected or predicted time of occurrence of at least one predetermined event in the cardiac cycle. The at least one sequence of trigger signals σ(t) which is generated by the trigger signal generator of the data processing unit 110 is provided to the speed command signal generator 120.

In a preferred embodiment and as illustrated in FIG. 3, the speed command signal generator 120 is configured to initialize the increase of the speed command signal $n_{VAD}^{set}(t)$ a predetermined time interval $\tau^{incr}(h)$ before a characteristic event of the cardiac cycle occurs, which is used as a basis for generating the sequence of trigger signals σ(t). This sequence of trigger signals σ(t) can be used to change the pump speed in a moderate manner to avoid suction, blood damage, etc., or to allow the pump speed increase in a timely manner to address the phase shift between a change in speed and the resulting change in pressure (compliance of vasculature and inertia of blood) for the systolic co-ejection.

In the example illustrated in FIG. 3, the starting time of contraction of the left ventricle is used as the characteristic time taken into account for the sequence of trigger signals σ(t) generated by the trigger signal generator. The contraction of the left ventricle starts immediately after the R-wave occurs in the corresponding ECG signal. Thus, the speed command signal generator 120 may be configured to derive a sequence of trigger signals σ(t) based on the ECG signal, which is provided to the data processing unit 110. The data processing unit 110 may be configured to receive the ECG signal from an (external) ECG device 320 and to generate the sequence of trigger signals σ(t) by means of the trigger signal generator.

As mentioned above, another measuring signal may be used by the data processing unit 110 for generating the sequence of trigger signals σ(t), showing e.g. the beginning of left atrial contraction which can be used as an event, the time of occurrence of which precedes the beginning of the systolic ejection phase. For example, in FIG. 3b) some characteristic values and times are marked as examples on the signal for the left ventricular pressure LVP(t), namely the minimum value $LVP_{min}(j)$, the maximum value $LVP_{max}(j)$, its maximum change over time $dLVP(j)/dt|_{max}$, and its minimum change over time $dLVP(j)/dt|_{min}$.

To sum up, the speed command signal generator 120 synchronizes the adjustment of the speed command signal $n_{VAD}^{set}(t)$ with the cardiac cycle by means of at least one sequence of trigger signals σ(t) which is provided by the data processing unit 110 such that the speed pulse is initialized before the beginning of ventricular contraction and/or the occurrence of the R-wave in the ECG signal.

The predetermined time interval $\tau^{incr}(h)$ for initializing the increase of the speed command signal $n_{VAD}^{set}(t)$ may be set, for example, to about $\tau^{incr}(h)=150$ ms, preferably $\tau^{incr}(h)=100$ ms, most preferably $\tau^{incr}(h) \leq 100$ ms before the associated characteristic event in the cardiac cycle. The inventors have further found that it can be ensured by the predetermined time interval $\tau^{incr}(h)$ that the blood flow is not accelerated too fast, which is assumed to reduce the likelihood of blood damage and/or of undesired hemodynamic effects. Thus, the speed command signal generator 120 is configured to adjust the speed command signal $n_{VAD}^{set}(t)$ such that the speed $n_{VAD}(t)$ of the VAD is altered smoothly.

As one particular example, FIG. 3d) shows a speed command signal $n_{VAD}^{set}(t)$ with a ramp for increasing or decreasing the speed $n_{VAD}(t)$ of the VAD linearly, but other forms may be possible as well, such as an exponential speed increase or decrease.

Finally, the speed command signal generator 120 is configured to adjust the speed $n_{VAD}(t)$ of the VAD back to the initial speed level $n_{VAD}^{set,basic}(t)$ to end a current speed pulse after the predetermined pulse duration $\Sigma^{pulse}$ (h).

Alternatively or additionally, the speed command signal generator 120 is configured to adjust the speed command signal $n_{VAD}^{set}(t)$ for altering the speed $n_{VAD}(t)$ of the VAD to end a current speed pulse when a predetermined characteristic event of the cardiac cycle occurs.

In a preferred embodiment, the predetermined event is the beginning of relaxation of the assisted heart and/or the closing of the aortic valve. Here, the predetermined time interval $\tau^{red}(h)$ for initializing the reduction of the speed command signal $n_{VAD}^{set}(t)$ before, during or after a predetermined characteristic event in the cardiac cycle may also be taken into account. Preferably, the trigger for terminating the speed pulse is part of the sequence of trigger signals σ(t) and is provided by the data processing unit 110 a time interval $\tau^{red}(h)$ before ventricular relaxation begins. Preferably, this trigger signal is based on a prediction of the beginning of ventricular relaxation detected during previous cardiac cycles.

For example, the closing of the aortic valve can be determined when the left ventricular pressure LVP(t) drops below the aortic pressure AoP(t) or, correspondingly, when the pressure difference between the inlet 54 and the outlet 56 of the flow cannula 53 becomes lower than zero.

The data processing unit 110 is further configured to derive the sequence of trigger signals σ(t) from at least one signal that comprises information relating to the closing of the aortic valve of the assisted heart as a characteristic event in the cardiac cycle.

For example, useful signals may be a measuring signal representing a left ventricular pressure LVP(t) of the assisted heart and/or the aortic pressure AoP(t) adjacent to the assisted heart. If the blood pump is configured for assistance of and placement into the right side of the heart, the signal may be a measuring signal representing a blood pressure in the vena cava CVP(t) adjacent to the assisted heart and/or right ventricular pressure RVP(t) and/or a blood pressure in the pulmonary artery PAP(t) adjacent to the assisted heart.

The data processing unit 110 is configured to derive a sequence of trigger signals σ(t) from a required motor current $I_{VAD}(t)$ that is provided by the speed control unit 130 to the rotary pumping device 50. As discussed elsewhere herein, the required motor current $I_{VAD}(t)$ reflects the energy required by the rotary pumping device 50 to follow the set speed value. Thus, the command signal generator 120 may be triggered by a corresponding sequence of trigger signals σ(t) provided by the data processing unit 110.

Preferably, the data processing unit 110 is configured to receive, store and analyze at least one measuring signal containing characteristic information of the circulatory system and of the cardiac cycle in order to predict at least one event per heartbeat based on analysis results of previous cardiac cycles. Most preferably, the data processing unit 110 is configured to analyze at least two measuring signals to filter the impact of the pump-induced pressure changes so that characteristic events in the cardiac cycle may be reliably detected.

The invention claimed is:

1. A control device for controlling a rotational speed $(n_{VAD}(t))$ of a non-pulsatile ventricular assist device (VAD), by an event-based within-a-beat control strategy, wherein the control device is configured to:
   alter the rotational speed $(n_{VAD}(t))$ of the VAD within a cardiac cycle of an assisted heart;
   derive at least one sequence of trigger signals (σ(t)) based on a signal representing an electrical current that is supplied to an actuator of the VAD, wherein the at least one sequence of trigger signals (σ(t)) is related to at least one predetermined characteristic event in the cardiac cycle, and
   synchronize the alteration of the rotational speed $(n_{VAD}(t))$ with a heartbeat by the at least one sequence of trigger signals (σ(t)),
   wherein the control device is further configured to control the rotational speed $(n_{VAD}(t))$ of the VAD such that, in a diastolic phase of the cardiac cycle of the assisted heart, an amount of blood ejected by the VAD into an artery of interest is such that a predetermined blood volume remains in a corresponding ventricle and co-ejection from the VAD and from the corresponding ventricle during systole results in a predetermined total peak blood flow $(Q_{total|max}(h))$.

2. The control device of claim 1, wherein the control device is further configured to alter the rotational speed $(n_{VAD}(t))$ of the VAD for a predetermined pulse duration $(\tau^{pulse}(h))$ or a heart rate dependent pulse duration $(\tau^{assist}(h))$ to restore and/or maintain at least a predetermined pulsatility $(\Delta \overline{AoP}(h))$ in the artery of interest within the cardiac cycle, and to synchronize at least one of a beginning and an end of the rotational speed alteration by the at least one sequence of trigger signals (σ(t)).

3. The control device of claim 2, wherein the control device is further configured to generate a speed command signal $(n_{VAD}^{set}(t))$ for the alteration of the rotational speed $(n_{VAD}(t))$ of the VAD so that the predetermined pulsatility $(\Delta \overline{AoP}(h))$ is achieved, in:
   a first setup by an open-loop control, wherein the speed command signal $(n_{VAD}^{set}(t))$ is alternated between predefined rotational speed levels using a command signal generator, or
   a second setup by a closed-loop assure control in a feedback system, wherein the speed command signal $(n_{VAD}^{set}(t))$ is automatically set for each heartbeat (h).

4. The control device of claim 3, wherein the control device is further configured to adjust the speed command signal $(n_{VAD}^{set}(t))$ to achieve the predetermined pulsatility $(\Delta \overline{AoP}(h))$ in the second setup.

5. The control device according to claim 2, wherein the control device is further configured to alter the rotational speed $(n_{VAD}(t))$ of the VAD to generate the predetermined pulsatility $(\Delta \overline{AoP}(h))$ only in y out of x consecutive cardiac cycles of the assisted heart, wherein x is an integer greater than 2 and y is an integer with y≤x.

6. The control device according to claim 5, wherein the control device is further configured to set the rotational speed $(n_{VAD}(t))$ of the VAD during at least y of the other x minus y consecutive cardiac cycles of the assisted heart, so that a mean arterial blood pressure per heartbeat $(\overline{AoP}(h))$ remains above a predetermined threshold value $(\overline{AoP}_{thr}(h))$.

7. The control device according to claim 2, wherein the control device is further configured to initialize an adjustment of a speed command signal $(n_{VAD}^{set}(t))$ a predetermined first time interval $(\tau^{iner}(h))$ before one of the at least one predetermined characteristic event occurs.

8. The control device according to claim 7, wherein the control device is further configured to end the adjustment of the speed command signal $(n_{VAD}^{set}(t))$ in accordance with at least one of: after the predetermined pulse duration $(\tau^{pulse}(h))$, after the heart rate dependent pulse duration $(\tau^{assist}(h))$, with an occurrence of one of the at least one predetermined characteristic event in the cardiac cycle, and a predetermined second time interval $(\tau^{red}(h))$ before or when the at least one predetermined event in the cardiac cycle occurs.

9. The control device according to claim 2, wherein the control device is further configured to adjust a speed command signal $(n_{VAD}^{set}(t))$ so that a mean arterial blood pressure per heartbeat $(\overline{AoP}(h))$ remains above a predetermined threshold value $(\overline{AoP}_{thr}(h))$.

10. The control device according to claim 1, wherein the control device is further configured to derive the at least one sequence of trigger signals (σ(t)) based on at least one measuring signal, the measuring signal representing at least one of the following physical quantities: a blood pressure difference between an outlet of the VAD for blood ejection and an inlet of the VAD for sucking blood in, a blood pressure in a ventricle of the assisted heart, a blood pressure in the aorta adjacent to the assisted heart, a blood pressure in the vena cava adjacent to the assisted heart, and a blood pressure in the pulmonary artery adjacent to the assisted heart.

11. The control device according to claim 10, wherein the control device is further configured to:
   determine, based on at least one of the at least one measuring signal characteristic information about the circulatory system within the cardiac cycle; and
   derive or predict the at least one predetermined characteristic event for an upcoming cardiac cycle based on characteristic information determined during previous cardiac cycles.

12. The control device according to claim 11, wherein the control device is further configured to determine from at least two measuring signals an impact of the alteration of the rotational speed ($n_{VAD}(t)$) of the VAD when deriving or predicting the at least one predetermined characteristic event.

13. The control device according to claim 1, wherein the control device is further configured to distinguish changes in the electrical current due to the alteration of the rotational speed ($n_{VAD}(t)$) of the VAD from changes in the electrical current caused by the assisted heart passing through the cardiac cycle.

14. The control device according to claim 1, wherein the artery of interest is the aorta or the pulmonary artery and the predetermined total peak blood flow ($Q_{total|max}(h)$) is at least 6 L/min.

15. The control device according to claim 1, wherein the control device is further configured to perform at least one of the following: increase the rotational speed ($n_{VAD}(t)$ of the VAD during systole of the assisted heart and/or reduce the rotational speed ($n_{VAD}(t)$) of the VAD during diastole of the heart.

16. The control device according to claim 1, wherein the control device is further configured to alter the rotational speed of the VAD only when an average VAD-induced blood flow can be set above a currently required minimum blood flow demand of the assisted heart.

17. The control device according to claim 1, wherein the at least one predetermined characteristic event is a beginning of ventricular contraction of the assisted heart.

18. The control device according to claim 1, wherein the at least one predetermined characteristic event in the cardiac cycle is at least one of a beginning of ventricular relaxation of the assisted heart and a closing of the aortic valve.

19. A non-pulsatile ventricular assist device (VAD) for assistance of a heart, comprising a control device for controlling a rotational speed ($n_{VAD}(t)$) of the VAD, by an event-based within-a-beat control strategy, wherein the control device is configured to:
   alter the rotational speed ($n_{VAD}(t)$) of the VAD within a cardiac cycle of an assisted heart;
   derive at least one sequence of trigger signals ($\sigma(t)$) based on a signal representing an electrical current that is supplied to an actuator of the VAD, wherein the at least one sequence of trigger signals ($\sigma(t)$) is related to at least one predetermined characteristic event in the cardiac cycle; and
   synchronize the alteration of the rotational speed ($n_{VAD}(t)$) with a heartbeat by the at least one sequence of trigger signals ($\sigma(t)$),
   wherein the control device is further configured to control the rotational speed ($n_{VAD}(t)$) of the VAD such that, in a diastolic phase of the cardiac cycle of the assisted heart, an amount of blood ejected by the VAD into an artery of interest is such that a predetermined blood volume remains in a corresponding ventricle and co-ejection from the VAD and from the corresponding ventricle during systole results in a predetermined total peak blood flow ($Q_{total|max}(h)$).

* * * * *